United States Patent [19]

Müller et al.

[11] Patent Number: 5,118,680

[45] Date of Patent: Jun. 2, 1992

[54] COMBATING ENDOPARASITES WITH 3-HYDROXYBENZOTHIOPHENES

[75] Inventors: Nikolaus Müller; Werner Hallenbach, both of Monheim; Achim Harder, Leverkusen; Werner Lindner, Cologne, all of Fed. Rep. of Germany

[73] Assignee: Bayer Aktiengesellschaft, Leverkusen, Fed. Rep. of Germany

[21] Appl. No.: 721,901

[22] Filed: Jun. 20, 1991

Related U.S. Application Data

[63] Continuation of Ser. No. 533,627, Jun. 5, 1990, abandoned.

[30] Foreign Application Priority Data

Jun. 20, 1989 [DE] Fed. Rep. of Germany ....... 3920087
Sep. 19, 1989 [DE] Fed. Rep. of Germany ....... 3931157

[51] Int. Cl.⁵ .................... A61K 31/38; A61K 413/02
[52] U.S. Cl. ............................. 514/233.5; 514/232.8; 514/253; 514/321; 514/324; 514/422; 514/443; 549/52; 549/55
[58] Field of Search .................. 514/232.8, 233.5, 253, 514/321, 324, 422, 443; 549/52, 55

[56] References Cited

U.S. PATENT DOCUMENTS

3,971,814  7/1976  Stoss et al. ..................... 549/55
4,800,211  1/1989  Tischler et al. ................. 514/443

Primary Examiner—Robert W. Ramsuer
Attorney, Agent, or Firm—Sprung Horn Kramer & Woods

[57] ABSTRACT

A method of combating endoparasites in humans and animals which comprises administering to such humans and animals an endoparasiticidally effective amount of a 3-hydroxybenzothiophene of the formula

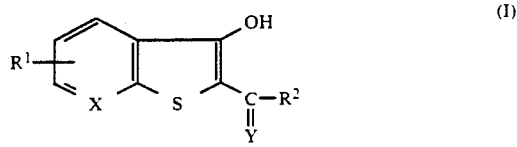

in which
  X represents =CH— or =N—,
  Y represents =O or =NH,
  $R^1$ represents one or more identical or different radicals from the group consisting of hydrogen, alkyl, alkoxy, alkylthio, halogenoalkyl, halogenoalkoxy, halogenoalkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, which, in turn, may again be substituted,
  $R^2$ represents optionally substituted alkoxy, cycloalkoxy or the radical $—NR^3R^4$,
  $R^3$ represents hydrogen or alkyl.
  $R^4$ represents an alkyl or carbocyclic or heterocyclic aromatic radical or the radical $—COOR^5$,
  $R^3$ and $R^4$, together with the adjacent nitrogen atom, represent a 5- or 6-membered heterocycle which may contain O or N as further heteroatoms and is optionally substituted by $C_1$–$C_4$-alkyl, $C_1$–$C_4$-hydroxyalkyl, $C_1$–$C_4$-halogenoalkyl or $C_1$–$C_4$-alkoxyalkyl
  $R^5$ represents alkyl, cycloalkyl, aralkyl or aryl, which, in turn, may again be substituted or optionally substituted aryl.

Many of the compounds are new, as well as their own intermediates.

5 Claims, No Drawings

COMBATING ENDOPARASITES WITH 3-HYDROXYBENZOTHIOPHENES

This application is a continuation of application Ser. No. 533,627, filed Jun. 5, 1990, now abandoned.

The present invention relates to the use of 3-hydroxybenzothiophenes for combating endoparasites, to new 3-hydroxybenzothiophenes and to processes for their preparation.

Substituted hydroxybenzothiophenes are already known. However, their use against endoparasites is not known (DE-OS (German Published Specification) 1,937,514, GB-PS 2,193,961, DOS (German Published Specification) 2,258,036).

The present invention relates to
1. the use of 3-hydroxybenzothiophenes of the formula (I)

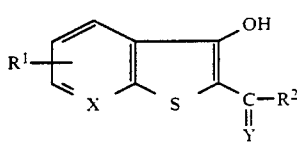

in which
X represents =CH— or =N—,
Y represents =O or =NH.
$R^1$ represents one or more identical or different radicals from the series comprising hydrogen, alkyl, alkoxy, alkylthio, halogenoalkyl, halogenoalkoxy, halogenoalkylthio, alkylenedioxy, halogenoalkylenedioxy, halogen, CN, NO$_2$, NH$_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, which, in turn, may again be substituted,
$R^2$ represents optionally substituted alkoxy, cycloalkoxy or the radical —NR$^3$R$^4$,
$R^3$ represents hydrogen or alkyl,
$R^4$ represents alkyl, or aralkyl, carbocyclic or heterocyclic aromatic radicals or the radical —COOR$^5$,
$R^3$ and $R^4$, together with the adjacent nitrogen atom, represent a 5- or 6-membered heterocycle which may contain O or N as further heteroatoms and is optionally substituted by C$_1$–C$_4$-alkyl, C$_1$–C$_4$-hydroxyalkyl, C$_1$–C$_4$-halogenoalkyl C$_1$–C$_4$-alkoxyalkyl or optionally substituted aryl
$R^5$ represents alkyl, cycloalkyl, aralkyl or aryl, which, in turn, may again be substituted,
for combating endoparasites in medicine and veterinary medicine.

The compounds of the formula I are known in some cases and can be prepared analogously to known processes.

2. New 3-hydroxybenzothiophenes of the formula (I)

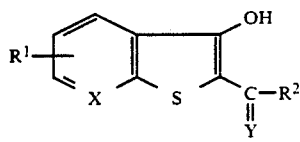

in which
X represents =N—,
Y represents =O or =NH, $R^1$ represents one or more identical or different radicals from the series comprising hydrogen, alkyl, alkoxy, alkylthio, halogenoalkyl, halogenoalkoxy, halogenoalkylthio, alkylenedioxy, halogenoalkylenedioxy, halogen, CN, NO$_2$, NH$_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, which, in turn, may again be substituted,
$R^2$ represents optionally substituted C$_{2-6}$-alkoxy, cycloalkoxy or the radical —NR$^3$R$^4$,
$R^3$ represents hydrogen or alkyl,
$R^4$ represents alkyl, aralkyl, carbocyclic or heterocyclic aromatic radicals,
$R^3$ and $R^4$, together with the adjacent nitrogen atom, represent a 5- or 6-membered heterocycle which may contain O or N as further hetero atoms and is optionally substituted by C$_1$–C$_4$-alkyl, C$_1$–C$_4$-hydroxyalkyl, C$_1$–C$_4$-halogenoalkyl C$_1$–C$_4$-alkoxyalkyl or optionally substituted aryl.

3. Process for the preparation of the new 3-hydroxybenzothiophenes of the formula (I)

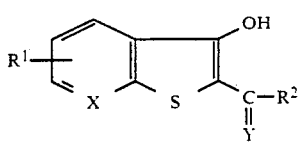

in which
X represents =N—,
Y represents =O or =NH,
$R^1$ represents one or more identical or different radicals from the series comprising hydrogen, alkyl, alkoxy, alkylthio, halogenoalkyl, halogenoalkoxy, halogenoalkylthio, alkylenedioxy, halogenoalkylenedioxy, halogen, CN, NO$_2$, NH$_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, which, in turn, may again be substituted,
$R^2$ represents optionally substituted C$_{2-6}$-alkoxy, cycloalkoxy or the radical —NR$^3$R$^4$,
$R^3$ represents hydrogen or alkyl,
$R^4$ represents alkyl, aralkyl, carbocyclic or heterocyclic aromatic radicals,
$R^3$ and $R^4$, together with the adjacent nitrogen atom, represent a 5- or 6-membered heterocycle which may contain O or N as further hetero atoms and is optionally substituted by C$_1$–C$_4$-alkyl, C$_1$–C$_4$-hydroxyalkyl, C$_1$–C$_4$-halogenoalkyl C$_1$–C$_4$-alkoxyalkyl or optionally substituted aryl characterized in that
a) compounds of the formula (II)

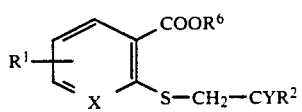

in which
X, Y, $R^1$ and $R^2$ have the abovementioned meanings, and
$R^6$ represents C$_{1-4}$-alkyl,
are heated in the presence of a base, or in that
b) compounds of the formula (III)

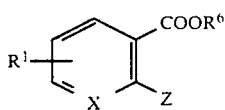

in which

X, $R^1$ and $R^6$ have the abovementioned meanings,
Y represents O, and
Z represents halogen,
are reacted with compounds of the formula (IV)

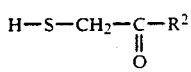

in which
$R^2$ has the abovementioned meaning, in the presence of a base.

4 New 3-hydroxybenzothiophenes of the formula (V)

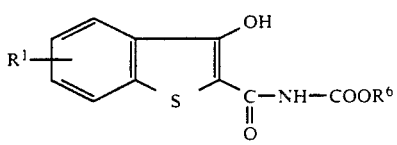

in which
$R^1$ represents one or more identical or different radicals from the series comprising hydrogen, alkyl, alkoxy, alkylthio, halogenoalkyl, halogenoalkoxy, halogenoalkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, which, in turn, may again be substituted.
$R^5$ represents alkyl, cycloalkyl, aralkyl or aryl, which, in turn, may again be substituted.

5. Process for the preparation of the new 3-hydroxybenzothiophenes of the formula (V)

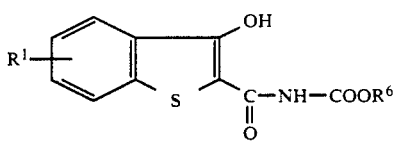

in which
$R^1$ represents one or more identical or different radicals from the series comprising hydrogen, alkyl, alkoxy, alkylthio, halogenoalkyl, halogenoalkoxy, halogenoalkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, which, in turn, ma again be substituted, and
$R^5$ represents alkyl, cycloalkyl, aralkyl or aryl, which, in turn, may again be substituted,
characterized in that
compounds of the formula (VI)

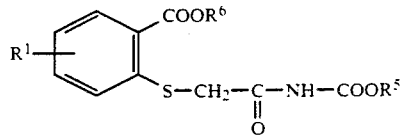

in which
$R^1$ and $R^5$ have the abovementioned meanings, and
$R^6$ represents $C_1$-$C_4$-alkyl, are heated in the presence of a base.

6. New compounds of the formula (VI)

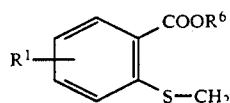

in which
$R^1$, $R^5$ and $R^6$ have the meanings mentioned in Item 5.

7. Process for the preparation of the compounds of the formula (VI) according to Item 6, characterized in that acid chlorides of the formula (VII)

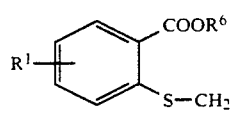

in which
$R^1$ and $R^6$ have the meanings mentioned in Item 6, are reacted with urethanes of the formula (VIII)

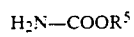

in which
$R^5$ has the meaning mentioned in Item 6.

8. Compounds of the formula (VII)

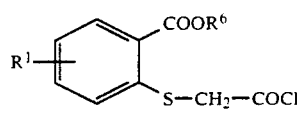

in which
$R^1$ and $R^6$ have the meanings mentioned in Item 6.

9. Process for the preparation of the compounds of the formula VII according to Item 8, characterized in that 3-(2 carboalkoxyphenyl)-thioglycolic acids of the formula (IX)

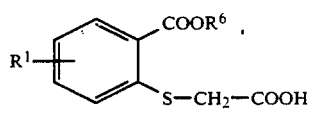

in which
$R^1$ and $R^6$ have the abovementioned meanings, are reacted with thionyl chloride, phosphorus trichloride or phosgene.

The compounds of the formula I are outstandingly suitable for combating end parasites, particularly in the field of veterinary medicine.

Preferred compounds of the formula I are those in which $R^1$ represents alkyl preferably having 1 to 4, in particular 1 or 2 carbon atoms, such as methyl, ethyl, n.- and i.-propyl and n.-, i.-, s.- and t.-butyl; alkoxy preferably having 1 to 4, in particular 1 or 2 carbon atoms, such as methoxy, ethoxy, n.- and i.- propyloxy and n.-, i.-, s.- and t.-butyloxy; alkylthio preferably having 1 to 4, in particular 1 or 2 carbon atoms, such as methylthio, ethylthio, n.- and i.-propylthio and n.-, i.-, s.- and t.-butylthio; halogenoalkyl preferably having 1 to 4, in particular 1 or 2 carbon atoms and preferably 1 to 5, in particular 1 to 3 halogen atoms, where the halogen atoms are identical or different and, as halogen atoms, preferably represent fluorine, chlorine or bromine, in particular fluorine, such as trifluoromethyl, fluoroethyl or chloroethyl; halogenoalkoxy preferably having 1 to 4, in particular 1 or 2 carbon atoms and preferably 1 to 5, in particular 1 to 3 halogen atoms, where the halogen atoms are identical or different and, as halogen atoms, preferably represent fluorine, chlorine, bromine, in particular fluorine, such as trifluoromethoxy; halogenoalkylthio preferably having 1 to 4, in particular 1 or 2 carbon atoms and preferably 1 to 5, in particular to 3 halogen atoms, where the halogen atoms are identical or different and, as halogen atoms, preferably represent fluorine, chlorine or bromine, in particular fluorine, such as trifluoromethylthio; in the case of phenyl, represents alkylenedioxy preferably having 1 or 2 carbon atoms such as methylenedioxy or ethylenedioxy; in the case of phenyl represents halogen-substituted alkylenedioxy preferably having 1 or 2 carbon atoms and preferably 1 to 4, in particular 2 to 3 halogen atoms, where the halogen atoms are identical or different and, as halogen atoms, preferably represent fluorine or chlorine, in particular fluorine, such as difluoromethylenedioxy, trifluoroethylenedioxy and tetrafluoroethylenedioxy. Further substituents are halogen, preferably fluorine, chlorine, bromine and iodine, in particular chlorine and bromine; cyano; nitro; dialkylamino preferably having 1 to 4, in particular 1 or 2 carbon atoms per alkyl group, such as dimethylamino, diethylamino or methyl-n-butylamino; alkylcarbonyl preferably having 2-4 carbon atoms; carbalkoxy preferably having 2 to 4, in particular 2 or 3 carbon atoms, such as carbomethoxy and carboethoxy; alkylsulphonyl preferably having 1 to 4, in particular 1 or 2 carbon atoms, such as methylsulphonyl and ethylsulphonyl; arylsulphonyl preferably having 6 or 10 aryl carbon atoms, such as phenylsulphonyl; phenyl, naphthyl, phenoxy, naphthoxy, phenylthio or naphthylthio, which, in turn, may again be substituted $R^2$ represents $C_{1-6}$-alkoxy which is optionally substituted by phenyl which, in turn, is optionally substituted by one of the radicals mentioned for $R^1$, represents $C_{3-7}$-cycloalkoxy or represents the radical —$NR^3R^4$, where $R^3$ represents hydrogen or alkyl, $R^4$ represents $C_{1-4}$-alkyl, benzyl or phenyl which are optionally substituted by one of the radicals mentioned for $R^1$, or represents a radical of the formula —$COOR^5$, $R^3$ and $R^4$, together with the adjacent nitrogen atom, represent a 5- or 6-membered heterocycle which may contain O or N as further hetero atoms and is optionally substituted by $C_4$-$C_7$-alkyl, $C_1$-$C_4$-hydroxyalkyl, $C_1$-$C_4$-halogenoalkyl, $C_1$-$C_4$-alkoxyalkyl, or optionally substituted phenyl, naphthyl, pyridyl, $R^5$ represents $C_1$-$C_4$-alkyl, $C_4$-$C_7$-cycloalkyl, aralkyl or aryl which, in turn, may be substituted by one of the radicals mentioned under $R^1$, X represents =Cl— or =N—, and Y represents =O or =NH.

Particularly preferred compounds of the formula I are those
in which $R^1$ represents halogen, in particular chlorine or fluorine, $C_1$-$C_4$-alkyl such as methyl or ethyl, $C_{1-4}$-alkoxy such as methoxy or ethoxy, $C_{1-4}$-halogenoalkoxy such as trifluoromethoxy, $C_{1-4}$-halogenoalkylthio such as trifluoromethylthio, phenyl which is optionally substituted, and further represents phenyl which is optionally substituted by $C_1$-$C_4$-alkyl, in particular methyl, $C_1$-$C_4$-alkoxy, in particular methoxy or ethoxy, $C_1$-$C_4$-halogenoalkoxy, in particular trifluoromethoxy or fluorochloroethoxy, $C_1$-$C_4$-halogenoalkylthio, in particular trifluoromethylthio or fluorochloromethylthio, $C_1$-$C_4$-alkylthio, in particular methylthio, halogenosulphonyl, in particular fluorosulphonyl or chlorosulphonyl, $C_1$-$C_4$-alkylsulphonyl, in particular methylsulphonyl, $C_1$-$C_4$-halogenoalkylsulphonyl, in particular trifluoromethylsulphonyl, $C_1$-$C_1$-halogenoalkyl, in particular trifluoromethyl, or methylenedioxy or ethylenedioxy which are optionally substituted by fluorine or chlorine, halogen, in particular fluorine or chlorine, $NO_2$, or phenoxy which is optionally substituted by one of the abovementioned radicals, $R^2$ represents $C_{1-4}$-alkoxy, cyclohexyloxy, benzyloxy, phenylethyloxy or phenylpropyloxy, where the phenyl radicals can optionally be substituted by one of the particularly preferred radicals mentioned for $R^1$, or represents the radical —$NR^3R^4$, where $R^3$ represents hydrogen, $R^4$ represents $C_{1-4}$-alkyl, benzyl or phenyl which are optionally substituted by one of the particularly preferred radicals mentioned for $R^1$ or represents a radical of the formula —$COOR^5$, $R^3$ and $R^4$, together with the adjacent nitrogen atom, represent one of the radicals piperidino, morpholino, pyrolidino, N-methylpiperazino or 2,6-dimethylmorpholino or 2,6-diphenylmorpholino $R^5$ represents $C_1$-alkyl or benzyl, X represents =CH— or =N—, and Y represents =O or =NH.

Very particularly preferred compounds of the formula (I) are those
in which $R^1$ represents halogen, in particular fluorine or chlorine, $NO_2$, $CF_3$, $CH_3$, $OCF_3$, $SCF_3$, $SCF_2Cl$, $OCH_3$, $OCF_2CF_2H$, —$OCF_2CHFO$—, —O—$CH_2$—O or —O—$CF_2$—O, $R^2$ represents $C_{1-4}$-alkoxy, cyclohexyloxy, benzyloxy, phenylethyloxy or phenylpropyloxy, where the phenyl radicals are optionally substituted by halogen, such as chlorine, or $C_{1-4}$-alkoxycarbonyl, or represents the radical —$NR^3R^4$, where $R^3$ represents hydrogen, $R^4$ represents methyl, ethyl, benzyl or phenyl which are optionally substituted by halogen such as chlorine, fluorine or bromine, $C_{1-4}$-alkyl such as methyl, $C_{1-4}$-halogenoalkyl such as trifluoromethyl, $C_{1-4}$-alkoxy such as methoxy, $C_{1-4}$-alkylmercapto such as methylmercapto, $C_{1-4}$-halogenoalkylmercapto such as trifluoromethylmercapto, or
$C_{1-4}$-alkoxycarbonyl such as methoxycarbonyl, or represents the radical $—COOR^5$, $R^3$ and $R^4$, together with the adjacent nitrogen atom, represent one of the radicals piperidino, morpholino N-methylpiperazine or 2,6-dimethylmorpholino $R^5$ represents $C_{1-4}$-alkyl or benzyl, X represents $=CH—$ or $=N—$, and Y represents $=O$ or $=NH$.

In particular, the following compounds of the formula (I) may be mentioned in which the radicals $R^1$, $R^2$ and X have the meanings indicated:

| X | $R^1$ | $R^2$ | Y |
|---|---|---|---|
| CH | H | $—OCH_3$ | O |
| " | " | $—OC_2H_5$ | " |
| " | " | $—OsC_4H_9$ | " |
| " | " | $—O—CH_2C_6H_5$ | " |
| " | " | $—O—CH_2-4ClC_6H_4$ | " |
| " | 5-Cl | $—OCH_3$ | " |
| " | " | $—OC_2H_5$ | " |
| " | " | $—O—CH_2C_6H_5$ | " |
| " | 5-NO_2 | $—OCH_3$ | " |
| " | " | $—O-iC_3H_7$ | " |
| " | 5-CF_3 | $—O—CH_3$ | " |
| " | " | $—O—CH_2C_6H_5$ | " |
| " | 4-Cl | $—O—C_2H_5$ | " |
| " | 5-NH_2 | $—O—CH_3$ | " |
| " | 5-NH—C(=O)—CH_3 | $—O—CH_3$ | " |
| " | H | $—NH-4-ClC_6H_4$ | " |
| " | " | $—NH-3-CF_3C_6H_4$ | " |
| " | 5-NO_2 | $—NH-3-ClC_6H_4$ | " |
| " | " | $—NH—C_6H_5$ | " |
| " | 5-CF_3 | $—NH-4-CH_3C_6H_4$ | " |
| N | H | $—OCH_3$ | " |
| " | " | $—OC_2H_5$ | " |
| N | " | $—O-nC_4H_9$ | O |
| " | " | $—O—CH_2C_6H_5$ | " |
| " | " | $—NH-4-ClC_6H_4$ | " |
| " | " | $—NH-3,4-Cl_2C_6H_3$ | " |
| " | 5-Cl | $—OCH_3$ | " |
| CH | H | $—NH—COOCH_3$ | " |
| " | -5-Cl | $—NH—COOC_2H_5$ | " |
| " | -5,6-Cl_2 | $—NH—COOCH_3$ | " |
| " | -5-COOCH_3 | $—NH—COOC_2H_5$ | " |
| " | -5-SO_2NH_2 | $—NH—COOC_2H_5$ | " |
| " | —H | $—NH—COOiC_3H_7$ | " |
| " | —H | $—NH—COOsC_4H_9$ | " |
| " | -5-Cl | $—NH—COOCH_2C_6H_5$ | " |
| " | -5-NO_2 | $—NH—COOCH_2C_6H_5$ | " |
| " | -5-CF_3 | $—NH—COOnC_3H_7$ | " |
| " | —H | $—OCH_3$ | NH |
| " | -5-Cl | $—OCH_3$ | " |
| " | -5-NO_2 | $—OC_2H_5$ | " |
| " | —H | $—OiC_3H_7$ | " |
| " | —H | $—OnC_4H_9$ | " |
| " | -5,6(CH_3)_2 | $—OsC_4H_9$ | " |
| " | —H | $—OCH_2C_6H_5$ | " |
| " | —H | (morpholino) | " |
| " | —H | $—N(C_2H_5)_2$ | " |

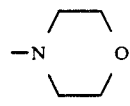

-continued

| X | $R^1$ | $R^2$ | Y |
|---|---|---|---|
| " | -5-Cl | (piperidino) | " |
| " | -5-CH_3 | (N-methylpiperazine) | " |
| " | —H | $—NH—C_6H_5$ | " |
| " | -5-Cl | $—NH-3,4-Cl_2C_6H_3$ | " |
| " | -5-NO_2 | $—NH-4-ClC_6H_4$ | " |
| " | —H | (2,6-diphenylmorpholino) | NH |
| " | 5-Cl | (2,6-diphenylmorpholino) | NH |
| " | —H | (2,6-diphenylmorpholino) | O |
| " | —H | (2,6-diphenylmorpholino) | NH |
| " | —H | (2-phenyl-6-methylmorpholino) | " |
| " | —H | (2,6-diphenylmorpholino) | O |
| N | —H | (2,6-diphenylmorpholino) | NH |
| N | —H | (2,6-diphenylmorpholino) | O |

If cyclohexyl S-(2-carbomethoxyphenyl)-thioglycolate is employed in process 3a) as the compound of the formula (II), the process can be represented by the following equation:

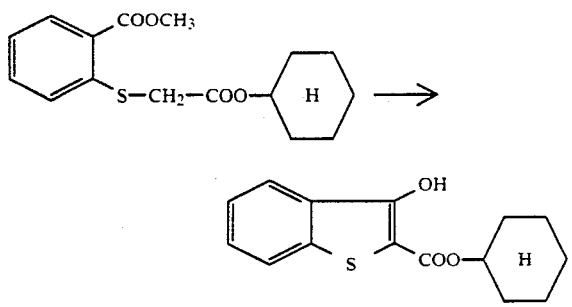

The compounds of the formula II are known in some cases. They can be prepared by processes which are known per se (Katz et. al., J. Org. Chem. 18 (1953), p 1380; DE-OS (German Published Specification) 1,937,514; A. D. Dunn et. al., J. Heterocycl. Chem. 24 (1987), p 85).

Preferably, compounds of the formula II are employed in which $R^1$, $R^2$ and X have the meanings indicated as preferred for the compounds of the formula (I) and $R^6$ represents methyl or ethyl.

In particular, the following compounds of the formula II may be mentioned: methyl S-(2-carbomethoxyphenyl)-thioglycolate, s-butyl S-(2-carbomethoxyphenyl)-thioglycolate, S-(2-carbomethoxyphenylthioglycolic acid anilide, S-(2-carboethoxyphenyl)-thioglycolic acid 4-chloroanilide, ethyl S-(2-carbomethoxy-5-chloro)-thioglycolate, methyl S-(2-carbomethoxyl-5-nitro)-thioglycolate, S-(2-carboethoxy-5-nitrophenyl)-thioglycolic acid p-toluidide, methyl S-(2-carboethoxy-5-trifluoromethylphenyl)-thioglycolate, benzyl S-(2-carbomethoxy-5,6-dichlorophenyl)thioglycolate, methyl 2-carbomethoxymethylthiopyridine-3-carboxylate, methyl 2-carbobenzyloxymethylthio-pyridine-3-carboxylate and methyl 2-(N-phenylcarbamoyl)-methylthiopyridine-3-carboxylate.

The reaction is carried out at temperatures of 20°–200° C., preferably at 50°–150° C., particularly preferably at the boiling point of the diluent.

Suitable diluents are all inert organic solvents. In particular, these include aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, in addition alcohols such as methanol, ethanol, isopropanol, butanol, in addition ethers such as diethyl ether and dibutyl ether, glycol dimethyl ether and diglycol dimethyl ether, tetrahydrofuran and dioxane, furthermore ketones, such as acetone, methyl ethyl ketone, methyl isopropyl ketone and methyl isobutyl ketone, additionally esters, such as methyl acetate and ethyl acetate, in addition nitriles, such as, for example, acetonitrile and propionitrile, benzonitrile, glutaronitrile, furthermore amides, such as, for example, dimethylformamide, dimethylacetamide and N-methylpyrrolidone, and also dimethyl sulphoxide, tetramethylene sulphone and hexamethylphosphoramide.

Suitable bases are inorganic and organic bases. The bases which may be mentioned are alkali metal and alkaline earth metal hydroxides, carbonates, hydrogencarbonates and alkoxides, in addition amines such as, in particular, tertiary amines, for example trimethylamine, triethylamine, N-methylmorpholine, pyridine, picolines, N-ethylpyrrolidine, diazabicyclo(4.3.0)-undecene(DBU), 1,4-diazabicyclo(2.2.2)octane (DABCO), diazabicyclo(3.2.0)nonene (DBN) and ethyl-diisopropylamine.

The compounds of the formulae II and the bases are employed in a ratio of 1:1 to 1:1.5 to one another. An approximately equimolar ratio is preferred.

After completion of the reaction, the diluent is distilled off in part (up to about 50%), aqueous acid is added to the residue and the compounds of the formula I are isolated in a manner known per se by extracting the with a suitable solvent, for example ether or methylene chloride. The compounds of the formula I can then be purified in a customary manner, for example by chromatography.

If ethyl 2-chloro-6-trifluoromethyl-nicotinate is employed in process 3b as the compound of the formula III and mercaptoacetic acid m-chloroanilide as the compound of the formula IV, the course of the reaction can be represented by the following equation:

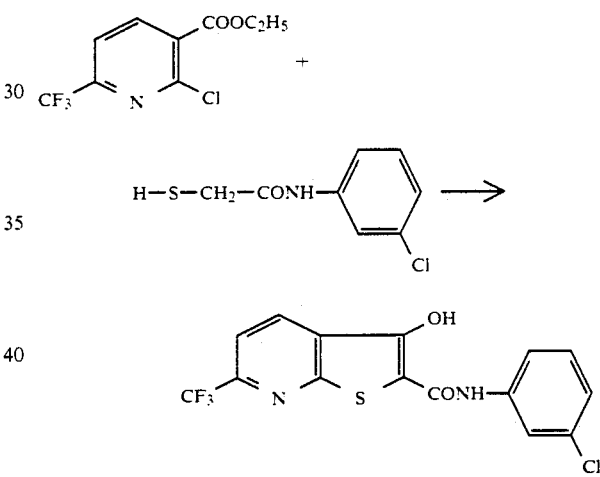

Preferably, compounds of the formulae III and IV are employed in which $R^1$, $R^2$, X and Y have the meanings indicated as preferred and particularly preferred for the compounds of the formula I and $R^6$ represents methyl or ethyl. The compounds of the formula III and IV are known or can be prepared analogously to known processes (DE-OS (German Published Specification) 1,937,514, Katz et. al., J. Org. Chem. 18 (1953), p. 1380, A. D. Dunn et. al., J. Heterocycl. Chem. 24 (1987) p. 85, J. Am. Chem. Soc. 69 (1947), p. 2914).

In particular, the following compounds of the formula III may be mentioned: methyl 2-chloro-5-nitrobenzoate, ethyl 2-chloro-5-nitrobenzoate, methyl 2-chloro-5-trifluoromethyl-benzoate, dimethyl 4-chloroisophthalate, 3-carbomethoxy-4-chlorodiphenyl sulphone, methyl 2-chloro-nicotinate, methyl 2,5-dichloronicotinate and ethyl 2,6-dichloronicotinate.

In particular, the following compounds of the formula IV may be mentioned: methyl, ethyl, iso-propyl, n-butyl, sec.butyl, tert.-butyl, benzyl and p-chlorobenzylthioglycolate, thioglycolic acid anilide, thioglycolic acid p-toluidide, thioglycolic acid p-chloroanilide, thioglycolic acid 3-trifluoromethylanilide, thioglycolic acid 3,4-dichloroanilide and thioglycolic acid p-anisidide.

Process 3b is carried out by first introducing the compounds of the formula IV in a solvent, adding an approximately equimolar amount of a base, and adding the compound of the formula III in an approximately equimolar amount. It is also possible in this step to isolate the open-chain compound of the formula II, the compound of the formula I can be obtained directly without isolation of the compound of the formula II by further adding a base in an approximately equimolar amount.

Possible bases and solvents are those mentioned for process 3a. In addition to the solvents mentioned there, aliphatic alcohols can also be used.

The reaction is carried out between 0° and 200° C., preferably between 10° and 100° C., particularly preferably at room temperature or the boiling point of the solvent employed. For working up, water is added to the reaction mixture, which is acidified, and the precipitate is filtered off or the mixture is extracted.

If S-(2-carbomethoxyphenyl)-thioglycolic acid (N-carboethoxy)-amide is employed in process (5) as the compound of the formula (VI), the process can be represented by the following equation:

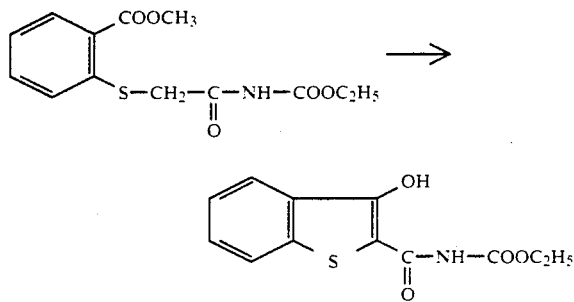

Preferably, compounds of the formula (VI) are employed in which $R^1$ and $R^5$ have the preferred meanings indicated for the compounds of the formula (I) and $R^6$ represents methyl or ethyl.

The following compounds of the formula (VI) may be mentioned in particular: S-(2-carbomethoxyphenyl)-thioglycolic acid (N-carboethoxy)-amide, S-(2-carbomethoxy-5-chlorophenyl)-thioglycolic acid (N-carbomethoxy)-amide, S-(2-carbomethoxy-5-nitrophenyl)-thioglycolic acid (N-carbomethoxy)-amide, S-(2-carboethoxy-5-trifluoromethyl(phenyl)-thioglycolic acid(N-carboethoxy)-amide, S-(2,5-dicarbomethoxyphenyl)-thioglycolic acid (N-carbomethoxy)-amide, S-(2-carbomethoxyphenyl)-thioglycolic acid (N-carbobenzyloxy)amide, S-(2-carbomethoxy-5-chlorophenyl)-thioglycolic acid (N-carbo-sec.-butyloxy)-amide, S-(2-carbomethoxy-5-methylphenyl)-thioglycolic acid (N-carbomethoxy)-amide.

The reaction is carried out at temperatures of 20°–200° C., preferably at 50°–150° C., particularly preferably at the boiling point of the diluent.

Suitable diluents are all inert organic solvents. In particular, these include aliphatic and aromatic, optionally halogenated hydrocarbons, such as pentane, hexane, heptane, cyclohexane, petroleum ether, benzine, ligroin, benzene, toluene, methylene chloride, ethylene chloride, chloroform, carbon tetrachloride, chlorobenzene and o-dichlorobenzene, in addition alcohols such as methanol, ethanol, isopropanol and butanol, in addition ethers such as diethyl ether and dibutyl ether, glycol dimethyl ether and diglycol dimethyl ether, tetrahydrofuran and dioxane, furthermore ketones, such as acetone, methyl ethyl ketone, methyl isopropyl ketone and methyl isobutyl ketone, additionally esters, such as methyl acetate and ethyl acetate, in addition nitriles, such as, for example, acetonitrile and propionitrile, benzonitrile and glutaronitrile, moreover amides, such as, for example, dimethylformamide, dimethylacetamide and N-methylpyrrolidone, and also dimethyl sulphoxide, tetramethylene sulphone and hexamethylphosphoramide.

Suitable bases are inorganic and organic bases. Bases which may be mentioned are alkali metal and alkaline earth metal hydroxides, carbonates, hydrogen carbonates, alkoxides, in addition amines such as, in particular, tertiary amines, for example trimethylamine, triethylamine, N-methylmorpholine, pyridine, picolines, N-ethylpyrrolidine, diazabicyclo(4.3.0)-undecene (DBU), 1,4-diazabicyclo(2.2.2)octane (DABCO), diazabicyclo(3.2.0)nonene (DBN) and ethyl-diisopropylamine.

The compounds of the formulae II and the bases are employed in a ratio of 1:1 to 1:1.5 to one another. An approximately equimolar ratio is preferred.

After completion of the reaction, the diluent is partly (up to about 50 %) removed by distillation, aqueous acid is added to the residue and the compounds of the formula I are isolated in a manner known per se, by extracting them with a suitable solvent, for example ether or methylene chloride. The compounds of the formula I can then be purified in a customary manner, for example by chromatography.

If S-(2-ethoxycarbonyl-3-chlorophenyl)-thioglycolyl chloride is employed as the compound of the formula (VII) and cyclopropylurethane as the urethane of the formula (VIII) in process (7) for the preparation of the compounds of the formula (VI), the process can be illustrated by the following equation:

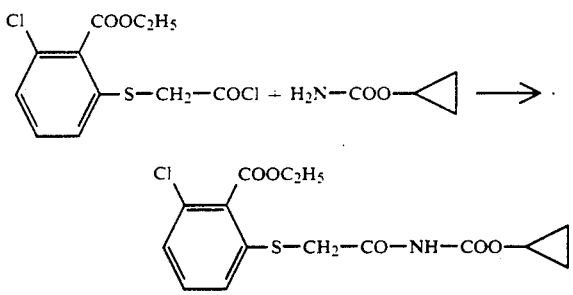

The compounds of the formula (VII) are new. Their preparation is described below. The following compounds of the formula (VII) may be mentioned particularly: S-(2-carbomethoxyphenyl)-thioglycolyl chloride, S-(4-chloro-2-carbomethoxyphenyl)-thioglycolyl chloride, S-(4,5-dichloro-2-carbomethoxyphenyl)-thioglycolyl chloride, S-(4-nitro-2-carboethoxyphenyl)-thioglycolyl chloride, S-(4-methyl-2-carbomethoxyphenyl)-thioglycolyl chloride and S-(4-sulphamoyl-2-carboethoxyphenyl)-thioglycolyl chloride.

Urethanes of the formula (VIII) are known. The following may be mentioned in particular: methylurethane, ethylurethane, propylurethane, i-propylurethane, s-butylurethane, benzylurethane, 2-chloroethylurethane, p-chlorobenzylurethane and 3,4-dichlorobenzylurethane.

The reaction is preferably carried out by adding together equimolar amounts of the compounds (VII) and (VIII) and heating.

The reaction temperature is between 20° and 200° C., preferably between 60° and 120° C.

The reaction is carried out at normal pressure or between 1.5 and 10 bar.

It may also be carried out in the presence of diluents.

If S-(2-methoxy-carbonyl-4-chloro-phenyl)-thioglycolic acid and thionyl chloride are employed in process (8) for the preparation of the compounds of the formula (VII), the course of the reaction can be represented as follows:

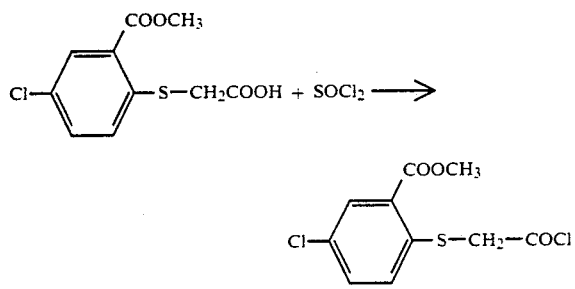

Compounds of the formula (IX) are known or can be prepared by known processes (compare Friedländer Liebigs Anm. Chem. 351 (1907), p. 390–420). The following may be mentioned individually: S-(2-carbomethoxyphenyl)-thioglycolic acid, S-(4-chloro-2-carbomethoxyphenyl)-thioglycolic acid, S-(4,5-dichloro-2-carboethoxyphenyl)-thioglycolic acid, S-(4-nitro-2-carbomethoxyphenyl)-thioglycolic acid and S-(4,5-dimethyl-2-carbomethoxyphenyl)-thioglycolic acid.

The reaction is carried out by bringing equimolar amounts of the compound of the formula (IX) to reaction with thionyl chloride at temperatures of 20° C. at 100° C. and pressures from normal pressure up to 3 bar. If appropriate, the reaction can also be carried out in the presence of a diluent.

The active compounds are suitable for combating pathogenic endoparasites which occur in humans or in the keeping and breeding of animals in the case of productive, breeding, zoo, laboratory, experimental and pet animals and have favourable toxicity to warm-blooded animals. In this connection, they are active against all or individual stages of development of the pests and against resistant and normally sensitive species. By combating the pathogenic endoparasites, disease, cases of death and yield reductions (for example in the production of meat, milk, wool, hides, eggs, honey, etc.) should be reduced so that more economical and simpler keeping of animals is possible by the use of the active compounds. The pathogenic endoparasites include cestodes, trematodes, nematodes and acantocephalae, in particular:

from the order of Pseudophyllidea, for example: Diphyllobothrium spp., Spirometra spp., Schistocephalus spp., Ligula spp., Bothridium spp. and Diphlogonoporus spp., from the order of Cyclophyllidea, for example: Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp. and Diplopylidium spp., from the subclass of Monogenea, for example: Gyrodactylus spp., Dactylogyrus spp. and Polystoma spp., from the subclass of Digenea, for example: Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp., Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp. Metorchis spp., Heterophyes spp. and Metagonimus spp., from the order of Enoplida, for example: Trichuris spp., Capillaria spp., Trichomosoides spp. and Trichinella spp., from the order of Rhabditia, for example: Micronema spp. and Strongyloides spp., from the order of Strongylida, for example: Stronylus spp., Triodontophorus spp., Oesophagodontus spp., Trichonema spp., Gyalocephalus spp., Cylindropharynx spp., Poteriostomum spp., Cyclococercus spp., Cylicostephanus spp., Oesophagostomum spp., Chabertia spp., Stephanurus spp., Ancylostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp. and Ollulanus spp., from the order of Oxyurida, for example: Oxyuris spp., Enterobius spp., Passalurus spp., Syphacia spp., Aspiculuris spp. and Heterakis spp., from the order of Ascaridia, for example: Ascaris spp., Toxascaris spp., Toxocara spp., Parascaris spp., Anisakis spp. and Ascaridia spp., from the order of Spirurida, for example: Gnathostoma spp., Physaloptera spp., Thelazia spp., Gongylonema spp., Habronema spp., Parabronema spp., Draschia spp. and Dracunculus spp., from the order of Filariida, for example: Stephanofilaria spp., Parafilaria spp., Setaria spp., Loa spp., Dirofilaria spp., Litomosoides spp., Brugia spp., Wuchereria spp. and Onchocerca spp., from the order of Gigantorhynchida, for example: Filicollis spp., Moniliformis spp., Macracanthorhynchus spp. and Prosthenorchis spp..

The productive and breeding animals include mammals such as, for example, cattle, horses, sheep, pigs, goats, camels, water buffalo, donkeys, rabbits, fallow deer, reindeer, animals with valuable fur such as, example, mink, chinchilla and racoons, bird such as, for example, hens, geese, turkeys and ducks, fresh and salt water fish, such as, for example, trout, carp and eels, reptiles and insects such as, for example, honey bees and silk worms.

The laboratory and experimental animals include mice, rats, guinea-pigs, golden hamsters, dogs and cats.

The pet animals include dogs and cats.

Administration can be carried out both prophylactically and therapeutically.

The active compounds are administered directly or enterally, parenterally, dermally or nasally in the form of suitable preparations, by treatment of the environment or with the aid of active compound-containing molded articles such as, for example, strips, sheets, tapes, neck bands, ear tags, limb bands and marking devices.

Enteral administration of the active compounds is carried out, for example, orally in the form of powders, tablets, capsules, pastes, drinks, granules, orally administrable solutions, suspensions and emulsions, boli, medicated feed or drinking water. Dermal administration is carried out, for example, in the form of dipping, spraying or pouring-on and spotting-on. Parenteral administration is carried out, for example, in the form of injection (intramuscular, subcutaneous, intravenous or intraperitoneal) or by implants.

Suitable preparations are:

solutions such as injection solutions, oral solutions, concentrates for oral administration after dilution, solutions for use on the skin or in body cavities, pouring-on formulations and gels;

emulsions and suspensions for oral or dermal administration and also for injection; semi-solid preparations;

formulations in which the active compound is processed in an ointment base or in an oil-in-water or water-in-oil emulsion base;

solid preparations such as powders, premixes or concentrates, granules, pellets, tablets, boli or capsules;

aerosols and inhalants, and active compound-containing moulded articles.

Injection solutions are administered intravenously, intramuscularly and subcutaneously.

Injection solutions are prepared by dissolving the active compound in a suitable solvent and adding additives such as solubilizers, acids, bases, buffer salts, antioxidants and preservatives if necessary. The solutions are sterile filtered and bottled.

Solvents which may be mentioned are: physiologically tolerated solvents such as water, alcohols such as ethanol, butanol, benzyl alcohol, glycerol, propylene glycol, polyethylene glycols, N-methyl-pyrrolidone, and mixtures thereof.

If appropriate, the active compounds may also be dissolved in physiologically tolerated vegetable or synthetic oils which are suitable for injection.

Solubilizers which may be mentioned are: solvents which promote the dissolution of the active compound in the principle solvent or prevent its precipitation. Examples are polyvinylpyrrolidone, polyoxyethylated castor oil and polyoxyethylated sorbitan esters.

Preservatives are: benzyl alcohol, trichlorobutanol, p-hydroxybenzoic acid esters and n-butanol.

Oral solutions are administered directly. Concentrates are administered orally after previously diluting to the concentration for administration. Oral solutions and concentrates are prepared as described above for the injection solutions, it being possible to dispense with sterile working.

Solutions for use on the skin are dripped on, painted on, rubbed in, sprayed on or sprinkled on. These solutions are prepared as described above for the injection solutions.

It may be advantageous to add thickeners in the preparation. Thickeners are: inorganic thickeners such as bentonites, colloidal silica, aluminium monostearate, organic thickeners such as cellulose derivatives, polyvinyl alcohols and their copolymers, acrylates and metacrylates.

Gels are applied to or painted onto the skin or introduced into body cavities. Gels are prepared by adding thickeners to solutions which have been prepared as described for injection solutions such that a clear substance having an ointment-like consistency results. Thickeners employed are the abovementioned thickeners.

Pouring-on formulations are poured onto or sprayed onto limited regions of the skin, the active compound penetrating the skin and acting systemically.

Pouring-on formulations are prepared by dissolving, suspending or emulsifying the active compound in suitable skin-compatible solvents or solvent mixtures. If appropriate, further auxiliaries such as colourants, absorption-promoting substances, antioxidants, light screens and adhesives are added.

Solvents which may be mentioned are: water, alkanols, glycols, polyethylene glycols, polypropylene glycols, glycerol, aromatic alcohols such as benzyl alcohol, phenylethanol, phenoxyethanol, esters such as ethyl acetate, butyl acetate, benzyl benzoate, ethers such as alkylene glycol alkyl ethers such as dipropylene glycol monomethyl ether or diethylene glycol mono-butyl ether, ketones such as acetone, methyl ethyl ketone, aromatic and/or aliphatic hydrocarbons, vegetable or synthetic oils, DMF, dimethylacetamide, N-methylpyrrolidone or 2,2-dimethyl-4-oxy-methylene-1,3-dioxolane.

Colorants are all colorants which can be dissolved or suspended and which are permitted for use on animals.

Absorption-promoting substances are, for example, DMSO, spreading oils such as isopropyl myristate, dipropylene glycol pelargonate, silicone oils, fatty acid esters, triglycerides and fatty alcohols.

Antioxidants are sulphites or metabisulphites such as potassium metabisulphite, ascorbic acid, butylhydroxytoluene, butylhydroxyanisole and tocopherol.

Light screens are, for example, novantisolic acid.

Adhesives are, for example, cellulose derivatives, starch derivatives, polyacrylates, and natural polymers such as alginates or gelatin.

Emulsions can be adminstered orally, dermally or as injections.

Emulsions are either of the water-in-oil type or the oil-in-water type.

They are prepared by dissolving the active compound either in the hydrophobic or the hydrophilic phase and homogenizing this with the solvent from the other phase with the aid of suitable emulsifiers and, if appropriate, other auxiliaries such as colorants, absorption-promoting substances, preservatives, antioxidants, light screens and viscosity-increasing substances.

Hydrophobic phases (oils) which may be mentioned are: paraffin oils, silicone oils, natural vegetable oils such as sesame oil, almond oil or castor oil, synthetic triglycerides such as caprylic/capric acid biglyceride, a triglyceride mixture with vegetable fatty acids of chain length $C_{8-12}$ or other specifically selected natural fatty acids, and partial glyceride mixtures of saturated or unsaturated mono- and diglycerides of $C_8/C_{10}$ fatty acids, possibly also containing hydroxyl groups.

Fatty acid esters such as ethyl stearate, di-nbutyryl adipate, hexyl laurate, dipropylene glycol pelargonate, esters of a branched fatty acid of medium chain length with saturated fatty alcohols of chain length $C_{16}$–$C_{18}$, isopropyl myristate, isopropyl palmitate, caprylic/capric acid esters of saturated fatty alcohols of chain length $C_{12}$–$C_{18}$, isopropyl stearate, oleyl oleate, decyl oleate, ethyl oleate, ethyl lactate, wax-like fatty acid esters such as synthetic duck coccygeal gland fat, dibutyl phthalate, diisopropyl adipate, ester mixtures related the latter, etc.

Fatty alcohols such as isotridecyl alcohol, 2-octyl-dodecanol, cetylstearyl alcohol and oleyl alcohol.

Fatty acids such as, for example, oleic acid and its mixtures.

Hydrophilic phases which may be mentioned are: water, alcohols such as, for example, propylene glycol, glycerol, sorbitol and their mixtures.

Emulsifiers which may be mentioned are: non-ionic surfactants, for example polyoxyethylated castor oil, polyoxyethylated sorbitan monooleate, sorbitan monostearate, glycerol monostearate, polyoxyethyl stearate and alkylphenol polyglycol ethers;

ampholytic surfactants such as di-Na N-lauryl-$\beta$-iminodipropionate or lecithin;

anionic surfactants, such as Na lauryl sulphate, fatty alcohol ether sulphates, mono/dialkylpolyglycol ether orthophosphoric acid ester monoethanolamine salt;

cationic surfactants such as cetyltrimethylammonium chloride.

Further auxiliaries which may be mentioned are: viscosity-increasing and emulsion-stabilizing substances such as carboxymethylcellulose, methylcellulose and other cellulose and starch derivatives, polyacrylates, alginates, gelatin, gum arabic, polyvinylpyrrolidone, polyvinyl alcohol, copolymers of methyl vinyl ether and maleic anhydride, polyethylene glycols, waxes, colloidal silica or mixtures of the substances mentioned.

Suspensions may be administered orally, dermally or as an injection. They are prepared by suspending the active compound in an excipient liquid, if appropriate with the addition of further auxiliaries such as wetting agents, colorants, absorption-promoting substances, preservatives, antioxidants and light screens.

Excipient liquids which may be mentioned are all homogeneous solvents and solvent mixtures.

Wetting agents (dispersing agents) which may be mentioned are the abovementioned surfactants.

Further auxiliaries which may be mentioned are the abovementioned.

Semi-solid preparations can be administered orally or dermally. They are differentiated from the suspensions and emulsions described above only by their higher viscosity.

In order to produce solid preparations, the active compound is mixed with suitable excipients, if appropriate with the addition of auxiliary substances, and brought into the desired form.

Excipients which may be mentioned are all physiologically tolerated solid inert substances. Those which are used are inorganic and organic substances. Inorganic substances are, for example, sodium chloride, carbonates such as calcium carbonate, hydrogen carbonates, aluminium oxides, silicic acids, aluminas, precipitated or colloidal silica and phosphates.

Organic substances are, for example, sugars, cellulose, foodstuffs and feeds such as milk powder, animal meals, cereal meals and shreds, and starches.

Auxiliaries are preservatives, antioxidants and colorants which have already been mentioned above.

Other suitable auxiliaries are lubricants and glidants such as, for example, magnesium stearate, stearic acid, talc, bentonites, disintegration-promoting substances such as starch or cross-linked polyvinylpyrrolidone, binders such as, for example, starch, gelatin or linear polyvinylpyrrolidone and dry binders such as microcrystalline cellulose.

The active compounds may also be present in the preparations in a mixture with synergists or with other active compounds which act against pathogenic endoparasites. These active compounds are, for example, L-2,3,5,6-tetrahydro-6-phenylimidazothiazole, benzimidazole carbamates, praziquantel, pyrantel and febantel.

Ready-to-use preparations contain the active compound in concentrations of 10 ppm –20 per cent by weight, preferably 0.1–10 per cent by weight.

Preparations which are diluted before use contain the active compound in concentrations of 0.5–90 percent by weight, preferably 5 to 50 per cent by weight.

In general it has proved advantageous to administer amounts of about 1 to about 100 mg of active compound per kg of body weight per day to attain effective results.

EXAMPLE A

In vivo nematode test

Trichostrongylus colubriformis/sheep

Sheep infected experimentally with Trichostrongylus colubriformis were treated after expiry of the prepatency period of the parasite. The active compounds were administered orally as the pure active compound in gelatin capsules.

The degree of action is determined by quantitatively counting the worm eggs excreted with the faeces before and after treatment.

A complete stop in the excretion of eggs after treatment means that the worms have been expelled or damaged such that they no longer produce eggs (effective dose).

Active compounds tested and effective doses can be seen from the following table.

| Active compound Example No. | Effective dose in mg/kg |
| --- | --- |
| 3 | 10 |
| 10 | 10 |
| 65 | 10 |
| 20 | 10 |
| 54 | 5 |
| 55 | 5 |
| 63 a | 25 |
| 69 | 10 |
| 72 | 10 |
| 79 | 10 |
| 80 | 10 |
| 84 | 10 |
| 87 | 10 |
| 95 | 10 |

EXAMPLE B

In vivo nematode test

Haemonchus contortus/sheep

Sheep infected experimentally with Haemonchus contortus were treated after expiry of the prepatency period of the parasite. The active compounds were administered orally as the pure active compound in gelatin capsules.

The degree of action is determined by quantitatively counting the worm eggs excreted with the faeces before and after treatment.

A complete stop in the excretion of eggs after treatment means that the worms have been expelled or damaged such that they no longer produce eggs (effective dose).

Active compounds tested and effective doses can be seen from the following table.

| Active compound Example No. | Effective dose in mg/kg |
| --- | --- |
| 7 | 5 |
| 9 | 5 |
| 11 | 25 |
| 39 | 10 |
| 64 | 5 |
| 56 | 2.5 |
| 63 a | 5 |
| 71 | 5 |
| 79 | 10 |
| 81 | 5 |
| 95 | 5 |

PREPARATION EXAMPLES

Example of processes 3a and 3b

Preparation of 3-hydroxy-2-(3-chlorophenylcarbamoyl)thieno-[2,3b1]-pyridine

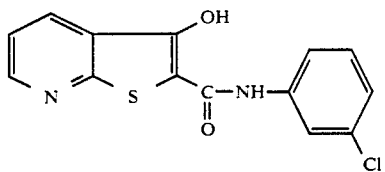

10.1 g (0.05 mol) of mercaptoacetic acid m-chloroanilide (prepared according to J. Am. Chem. Soc. 69 (1947), p. 2314) are initially introduced at room temperature in 100 ml of methanol and 2.7 g (0.05 mol) of sodium methoxide are added. The mixture is subsequently stirred at room temperature for 10 minutes and then 8.6 g (0.05 mol) of methyl 2-chloronicotinate are added. After subsequently stirring at room temperature for 1 hour, a further 4.1 g (0.075 mol) of sodium methoxide are added and the mixture is stirred at room temperature overnight. It is poured into 500 ml of water, the mixture is rendered acidic with acetic acid and the precipitate is filtered off and purified by digesting with hot toluene. 4.7 g (31 % of theory) of the product of melting point 247° C. are obtained.

Preparation of 3-hydroxybenzothiophene-2-carboxanilide

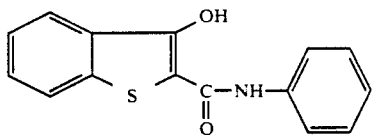

5.6 g (20.8 mmol) of S-(2-carbomethoxyphenylthio-glycolic acid anilide are dissolved in 100 ml of dry toluene and 3.2 g (21 mmol) of DBU are added. The mixture is heated to reflux and toluene is slowly removed by distillation at the same time. After reaction is complete, the mixture is partitioned between 100 ml of dilute HCl solution and dichloromethane. The solid intermediate phase resulting in this way is filtered off with suction and dried.

Yield: 3.23 g

Melting point: 229° C. (decomposition)

Preparation of benzyl 3-hydroxybenzothiophene-2-carboxylate

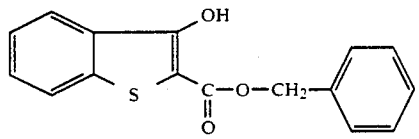

5 g (15.8 mmol) of benzyl S-(2-carbomethoxyphenyl)-thioglycolate and 3 g (19.7 mmol) of diazabicycloundecene are heated under reflux in 100 ml of toluene. At the same time, about 50 ml of toluene are removed by distillation in the course of one hour. After cooling, the mixture is poured into 2 N HCl and extracted with $CH_2Cl_2$. The residue is purified by filtration through silica gel using toluene as the eluent.

Yield: 2.6 g (58 % of theory)

Melting point: 81° C.

Preparation of

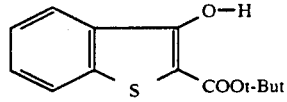

6.72 g (0.04 mol) of methyl 2-mercaptobenzoate and 6.02 g (0.04 mol) of tert.-butyl chloroacetate are initially introduced in 30 ml of dry methanol. A solution of 4.32 g (0.08 mol) of sodium methoxide in 30 ml of dry methanol is slowly added dropwise to this mixture, which is stirred until reaction is complete. The mixture is then evaporated in vacuo. The residue is partitioned between water and dichloromethane, and the organic phase is separated off, dried with $Na_2SO_4$ and evaporated in vacuo.

Yield: 9.6 g; melting point: 163° C.

The following compounds are prepared analogously:

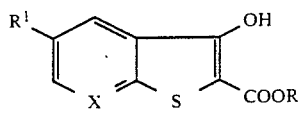

| Ex. No. | X | R¹ | R | m.p. [°C.] |
|---|---|---|---|---|
| 1 | N | H | CH₃ | 144 |
| 2 | N | H | C₂H₅ | 62 |
| 3 | CH | NO₂ | CH₃ | 215 |
| 4 | CH | NO₂ | —CH₂—C₆H₅ | 158 |
| 5 | CH | NO₂ | —C₂H₅ | 176 |
| 6 | CH | CF₃ | —CH₃ | 121 |
| 7 | CH | H | —CH₃ | 104 |
| 8 | CH | H | -i-C₃H₇ | ¹HNMR(CDCl₃) δ[ppm]: 7.92(d. 1H), 7.72(d. 1H), 7.5(t. 1H), 7.4, (t. 1H), 5.3, (m, 1H), 1.4, (d. 6H) |
| 9 | CH | H | -s-C₄H₉ | 81 |
| 10 | CH | H | —CH₂—C₆H₆ | 106 |
| 11 | CH | H | —CH₂—CH₂—C₆H₅ | |
| 12 | CH | H | —(CH₂)₃—C₆H₅ | ¹HNMR(CDCl₃) δ[ppm]: 7.95(d. 1H), 7.75(d. 1H), 7.5(t. 1H), 7.4, (t. 1H), 7.1–7.35(m, 5H), 4.38(t. 2H), 2.29(t. 2H), 2.0–2.2(m. 2H) |
| 13 | CH | H | cyclohexyl | 69 |
| 14 | CH | H | —CH₂—C₆H₄—Cl (4-Cl) | 124 |
| 15 | CH | H | —CH₂—C₆H₄—COOCH₃ | 104 |
| 16 | CH | H | —CH₂—C₆H₄—Cl (3-Cl) | 134 |
| 17 | CH | H | n-C₄H₉ | 77 |
| 18 | CH | H | i-C₄H₉ | 81 |
| 19 | CH | H | —CH(CH₃)—C₆H₅ | 88 |

| Ex. No. | X | R¹ | R³ | m.p. [°C.] |
|---|---|---|---|---|
| 20 | CH | —Br | —CH₃ | 174 |
| 21 | CH | —Br | —C₂H₅ | 99 |
| 22 | CH | —SO₂NH₂ | —CH₃ | >260 |
| 23 | CH | —CF₃ | —C₂H₅ | 100 |
| 24 | CH | —NO₂ | s-C₄H₉ | 119 |
| 25 | CH | —NO₂ | i-C₃H₇ | 209 |
| 26 | CH | —COOCH₃ | —CH₃ | 171 |
| 27 | CH | —NO₂ | -n-C₄H₉ | 117 |
| 28 | CH | —COOC₂H₅ | —C₂H₅ | 82 |
| 28a | CH | 5-Cl | —CH₃ | 141 |
| 28b | CH | 5-Cl | —C₂H₅ | 103 |
| 28c | CH | 6-Cl | —CH₂-Phenyl | 94 |
| 28d | CH | 5-CH₃ | —CH₃ | 74 |
| 28e | CH | 5-CH₃ | —C₂H₅ | 64 |
| 28f | CH | 5-CH₃ | —CH₂-Phenyl | 79 |
| 28g | CH | H | cyclopentyl  | 207 |

-continued

| Ex. No. | X | R¹ | R³ | m.p. [°C.] |
|---|---|---|---|---|
| 28h | CH | 5-Cl | 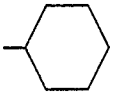 | >250° C. |

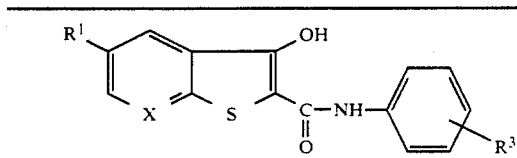

| Ex. No. | X | R¹ | R³ | m.p. [°C.] |
|---|---|---|---|---|
| 29 | N | —H | —H | 241 |
| 30 | N | —H | -3-Cl | 247 |
| 31 | CH | —NO₂ | —H | 239 |
| 32 | CH | —NO₂ | -3-Cl | 230 |
| 33 | CH | —NO₂ | -4-Cl | 257 |
| 34 | CH | —NO₂ | -4-F | 248–254 |
| 35 | CH | —NO₂ | -4-OCH₃ | 228 |
| 36 | CH | —NO₂ | -3-CH₃ | 189 |
| 37 | CH | —NO₂ | -4-CH₃ | 223 |
| 38 | CH | —CF₃ | —H | 197 |
| 39 | CH | —NO₂ | -3-CF₃ | 202 |
| 40 | N | —H | -4-CH₃ | 259 |
| 41 | N | —H | -4-Cl | 270 |
| 42 | CH | —H | -3-Cl | 221 |
| 43 | CH | —H | —H | 229 |
| 44 | CH | —H | -4-SCF₃ | 213 |
| 45 | CH | —H | -4-CF₃ | 200 |
| 46 | CH | —H | -4-Cl | 230 |
| 47 | CH | —Br | -3-CF₃ | 178 |
| 48 | CH | —H | -3-CH₃ | 193 |
| 49 | CH | 5-COOCH₃ | 4-CH₃ | 208 |
| 50 | CH | 5-COOCH₃ | 4-OCH₃ | 194 |
| 51 | CH | 5-COOCH₃ | —H | 233 |
| 52 | CH | 5-COOCH₃ | -3-CH₃ | 179 |
| 53 | CH | 5-COOCH₃ | -4-Cl | 135 |
| 54 | CH | 5-COOCH₃ | -3-CF₃ | 196 |
| 55 | CH | 5-COOCH₃ | -3-Cl | 223–227 |
| 55a | CH | H | -4-OCH₃ | 187 |

Preparation of
3-hydroxy-5-nitro-benzothiophene-2-carboxylic acid
N-(carboethoxy)-amide Example 56

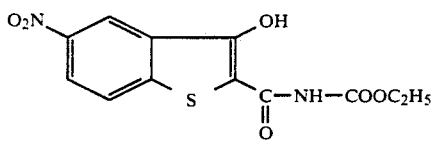

6.8 g (0.02 mol) of S-(2-carbomethoxy-5-nitrophenyl)-thioglycolic acid N-(carboethoxy)-amide are added to a solution of 0.98 g (0.025 mol) of sodium in 100 ml of ethanol and the mixture obtained is stirred at room temperature for 12 hours. It is then poured into 500 ml of water with stirring, the mixture is adjusted to pH 4 using 10 % strength hydrochloric acid and the precipitated solid is filtered off with suction, washed with water on the suction filter and dried. The product is virtually analytically pure.

Yield 4.5 g (73 % of theory); m.p. 259° C.

The S-(2-carbomethoxy-5-nitrophenyl)-thioglycolic acid N-(carboethoxy)-amide required as the starting material is obtained as follows:

7.3 g (0.025 mol) of S-(2-carbomethoxy-5-nitrophenyl)-thioglycolyl chloride and 2.5 g (0.0275 mol) of ethylurethane are heated at 80°–90° C. for 6 hours. After cooling, the solidified material is pulverized in a mortar and washed with 500 ml of water, the suspension is filtered off with suction, and the precipitate is washed with water, boiled in 300 ml of ethanol, cooled and filtered off with suction again. The product is washed on the suction filter and dried. The yield is 4 g (47% of theory) with a purity of 97.5% (HPC).

The following examples are prepared by process 5:

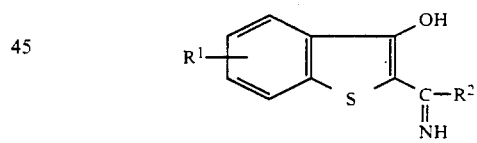

| Ex. No. | R¹ | R⁵ | m.p. °C. |
|---|---|---|---|
| 57 | —H | —CH₃ | >270 |
| 58 | —H | -n-C₄H₉ | 113° C. (dec.) |
| 59 | —H | —CH₂—C₆H₅ | 154° C. (dec.) |
| 60 | -5-COOCH₃ | —CH₂—C₆H₅ | 158° C. (dec.) |
| 61 | -5-COOCH₃ | -n-C₄H₉ | 144° C. (dec.) |
| 62 | -5-COOCH₃ | —C₂H₅ | 173° C. (dec.) |
| 63 | -5-COOCH₃ | —CH₃ | 251° C. |

| Ex. No. | X | R¹ | R⁵ | m.p. °C. |
|---|---|---|---|---|
| 63a | CH | 5-NO₂ | —C₂H₅ | 259 |
| 63b | CH | H | —C₂H₅ | 260 |
| 63c | CH | 5-Cl | —CH₃ | 250 (dec.) |
| 63d | CH | 5-CH₃ | —CH₃ | >265 |
| 63e | CH | 5-CH₃ | C₂H₅ | >265 |
| 63f | CH | 5-CH₃ | n-C₄H₉ | 92 |
| 63g | CH | 5-CH₃ | —CH₂-Phenyl | 133 |
| 63h | N | H | C₂H₅ | >250 |

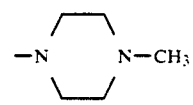

| Ex. No. | R¹ | R² | m.p. [°C.] |
|---|---|---|---|
| 64 | H | —OCH₃ | 195° C. |
| 65 | " | —O-sC₄H₉ | 196° C. |
| 66 | " | —OC₂H₅ | 186° C. |
| 67 | " | —O-iC₃H₇ | 234° C. |
| 68 | " | —O-nC₄H₉ | 181° C. |
| 69 | " | —NH—C₆H₅ | 224° C. |
| 70 | " | —NH-4-ClC₆H₄ | 265–270° C. |
| 71 | " | —N(C₂H₅)₂ | 142° C. |
| 72 | " | —NH-3CF₃C₆H₄ | 227° C. |
| 73 | " | —NH-3ClC₆H₄ | 209° C. |
| 74 | " | —NH-4COOCH₃C₆H₄ | >270° C. |
| 75 | " | —NH—CH₂—C₆H₅ | 224° C. |
| 76 | " | —NH—CH₂-3CF₃C₆H₄ | 237° C. |
| 77 | " | —N⟨ ⟩N—CH₃ | 140° C. |

-continued

Structure: benzothiophene with R¹ on benzene ring, 3-OH, 2-position C(=NH)-R²

| Ex. No. | R¹ | R² | m.p. [°C.] |
|---|---|---|---|
| 78 | " | -N(morpholine) | 147° C. |
| 79 | H | -N(piperidine) | 161° C. |
| 80 | " | -N(pyrrolidine) | 248° C. |
| 81 | " | -N(2,6-dimethylmorpholine) | 172° C. |
| 82 | " | -NH-CH₂-4-ClC₆H₄ | 221° C. |

Structure: thieno-pyridine with R¹, X, 3-OH, 2-position C(=NH)-R²

| Ex. No. | X | R¹ | R² | m.p. [°C.] |
|---|---|---|---|---|
| 83 | CH | 6-Cl | O-CH₃ | 213 |
| 84 | CH | 6-Cl | O-(CH₂)₂-CH₃ | 238 |
| 85 | CH | 6-Cl | -O-i-C₃H₇ | 220 |
| 86 | CH | 6-Cl | -O-s-C₄H₉ | 218 |
| 87 | CH | 5-CH₃ | -O-CH₃ | 243 |
| 88 | CH | 5-CH₃ | -O-(CH₂)₂-CH₃ | 224 |
| 89 | CH | 5-CH₃ | -O-n-C₄H₉ | 196 |
| 90 | CH | 5-CH₃ | -O-s-C₄H₉ | 171 |
| 91 | CH | 5-Cl | -O-CH₃ | 248 |
| 92 | CH | 5-Cl | -O-C₂H₅ | 232 |
| 93 | CH | 5-Cl | -O-n-C₃H₇ | 224 |
| 94 | CH | 5-Cl | -O-i-C₃H₇ | 207 |
| 95 | CH | 5-Cl | -O-s-C₄H₉ | 129 |
| 96 | CH | 6-Cl | -O-C₂H₅ | 224 |
| 97 | CH | 5-CH₃ | -O-C₂H₅ | 234 |
| 98 | CH | 5-Cl | -O-CH₂-C₆H₄ | 94 |
| 99 | CH | H | -O-CH₂-C₅H₉ | 207 |
| 100 | CH | 5-Cl | -O-CH₃-C₅H₉ | 187 |
| 101 | CH | 5-CH₃ | -N(H)-2-Cl-C₆H₄ | 184 |
| 102 | CH | 5-CH₃ | -N(H)-3-Cl-C₆H₄ | 207 |
| 103 | CH | 5-CH₃ | -N(H)-4-Cl-C₆H₄ | 261 |

-continued

| Ex. No. | X | R¹ | R² | m.p. [°C.] |
|---|---|---|---|---|
| 104 | CH | 5-Cl | -N(H)-2-Cl-C₆H₄ | 258 |
| 105 | CH | 5-Cl | -N(H)-2-Cl-C₆H₄ | 208 |
| 106 | CH | 5-Cl | -N(H)-4-Cl-C₆H₄ | >260 |
| 107 | CH | 6-Cl | -N(H)-2-Cl-C₆H₄ | 214 |
| 108 | CH | 6-Cl | -N(H)-3-Cl-C₆H₄ | 203 |
| 109 | CH | 6-Cl | -N(H)-3-Cl-C₆H₄ | 241 |
| 110 | CH | 6-Cl | -N(H)-3-CH₃-C₆H₄ | 218 |
| 111 | CH | 6-Cl | -N(H)-4-CH₃-C₆H₄ | 253 |
| 112 | CH | 6-Cl | -N(H)-3-CH₃-C₆H₄ | 197 |
| 113 | CH | H | -N(H)-CH(CH₃)-C₆H₄ | 161 |
| 114 | CH | 5-CH₃ | -NH-3-CH₃-C₆H₄ | 177 |
| 115 | CH | 5-CH₃ | -NH-2-CH₃-C₆H₄ | 194 |
| 116 | CH | 5-Cl | -NH-2-CH₃-C₆H₄ | 253 |
| 117 | CH | 5-Cl | -NH-3-CH₃-C₆H₄ | 217 |
| 118 | CH | 5-Cl | -NH-4-CH₃-C₆H₄ | 282 |
| 119 | CH | 5-Cl | -NH-3-CF₃-C₆H₄ | 216 |
| 120 | CH | 5-Cl | -NH-4-OCH₃-C₆H₄ | 274 |
| 121 | CH | H | -NH-4-F-C₆H₄ | 284 |
| 122 | CH | 5-Cl | -N(piperazine)-N-CH₃ | 151 |
| 123 | CH | 5-Cl | NH-CH(CH₃)-C₆H₄ | 193 |
| 124 | CH | 5-CH₃ | -NH-3-CF₃-C₆H₄ | 189 |
| 125 | CH | 5-CH₃ | -NH-4-OCF₃-C₆H₄ | 222 |
| 126 | CH | 5-CH₃ | -NH-4-F-C₆H₄ | 265 |
| 127 | CH | 5-CH₃ | -NH-CH(CH₃)-C₆H | 87 |
| 128 | CH | 5-CH₃ | -N(piperidine) | 188 |
| 129 | CH | 5-Cl | -N(piperidine) | >265 |
| 130 | CH | 5-CH₃ | -N(piperazine)-N-CH₃ | 177 |

-continued

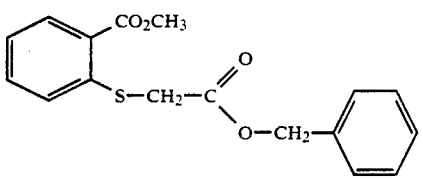

| Ex. No. | X | R¹ | R² | m.p. [°C.] |
|---|---|---|---|---|
| 131 | CH | 5-CH₃ | —N(piperidine) | 188 |
| 132 | CH | 5-CH₃ | —N(piperidine) | 269 |
| 133 | CH | 5-CH₃ | —N(morpholine) | 203 |
| 134 | CH | 5-CH₃ | —N(2,6-dimethylpiperidine) | 168 |
| 135 | N | H | —OCH₃ | >250 |
| 136 | N | H | —OC₂H₅ | 124 |
| 137 | N | H | —O-n-C₃H₇ | 184 |
| 138 | N | H | —O-i-C₃H₇ | 169 |
| 139 | N | H | —O-n-C₄H₇ | 188 |
| 140 | N | H | —O-s-C₄H₉ | 173 |
| 141 | N | H | —NH-3-Cl—C₆H₄ | >250 |
| 142 | N | H | —NH-4-Cl—C₆H₄ | >250 |
| 143 | N | H | —NH-4-CH₃—C₆H₄ | >260 |
| 144 | N | H | —NH-3-CH₃C₆H₄ | 251 |
| 145 | N | H | —NH-3-CH₃—C₆H₄ | 257 |
| 146 | N | H | —NH-4-F—C₆H₄ | 269 |
| 147 | CH | 5-CH₃ | —NH-4-CH₃C₆H₄ | 227 |

Examples of the preparation of the starting materials of the formula (II):

Preparation of benzyl 5-(2-carbomethoxyphenyl)thioglycolate

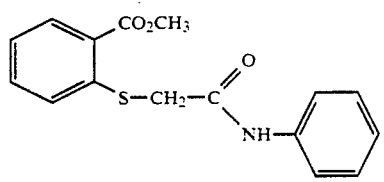

5 g (0.02 mol) of S-(2-carbomethoxyphenyl)-thioglycolyl chloride, dissolved in 50 ml of abs. CHCl₃, are added dropwise with cooling to a mixture of 2.2 g (0.02 mol) of benzyl alcohol, 2.8 ml (0.02 mol) of Et₃N and 50 ml of abs. CHCl₃. The mixture is stirred for a further hour, then the whole mixture is poured into a 5 per cent strength aqueous NaH₂PO₄ solution. The organic phase is separated off, and the aqueous phase is extracted again with CHCl₃, dried with Na₂SO₄ and evaporated. For purification, it is filtered through silica gel using dichloromethane.

Yield: 3.5 g of oil (54% of theory)

The product can also be employed crude in the next step.

¹H—NMR(CDCl₃): 7.95 ppm (dd, 1H, H$_{arom}$), 7.1-7.4 ppm (m, 8H, H$_{arom}$), 5.15 ppm (s, 2H, —CH₂—Ar), 3.9 ppm (s, 3H, O—CH₃), 3.77 ppm (s, 2H, —SCH₂—COO—)

Preparation of S-(2-carbomethoxphenyl)-thioglycolic acid anilide 1.85 ml (20 mmol) of aniline are initially introduced in 20 ml of abs. chloroform and 2.44 g (10 mmol) of S-(2-carbomethoxyphenyl)-thioglycolyl chloride, dissolved in 10 ml of abs. chloroform, are added dropwise with ice cooling. The mixture is subsequently stirred for one hour, then 100 ml of water are added. The organic phase is separated off and washed successively with 5% strength H₂SO₄, water and NaHCO₃ solution. It is dried using Na₂SO₄ and evaporated.

Yield: 3.57 g
Purity: 90.8% (GC/MS)

1H—NMR(CDCl₃): 8.7 ppm (5, 1H, NH), 8.0 ppm (dd, 1H, H$_{arom}$), 7.0-7.5 ppm (m, 8H, H$_{arom}$), 3.95 ppm (s, 3H, —OCH₃), 3.87 ppm (s, 2H, —SCH₂—CONH)

The following are prepared analogously:

| | | | physical data |
|---|---|---|---|
| | X | R¹ | ¹H-NMR(CDCl₃): δ[ppm] |
| d | O | —CH(CH₃)₂ | 7.99(d, 1H), 7.35-7.5 (m, 2H), 7.2(t, 1H), 4.95-5.1(m, 1H), 3.92(s, 3H), 3.68(s, 2H), 1.22(d, 6H) |
| e | O | —CH(CH₃)Et | 7.98(d, 1H), 7.35-7.5 (m, 2H), 7.19(t, 1H), 4.8-4.95(m, 1H), 3.92 (s, 3H), 3.71(s, 2H), 1.42-1.68(m, 2H), 1.2 (d, 3H), 0.85(t, 3H) |
| f | O | —CH₂—C₆H₅ | 7.98(d, 1H), 7.22-742 (m, 7H), 7.2(t, 1H), 5.16(s, 2H), 3.9(s, 3H), 3.75(s, 2H) |
| g | O | —C₆H₅ | melting point: 75° C. |

-continued

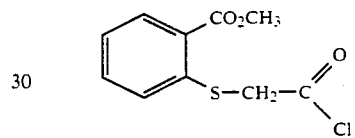

| | X | R¹ | physical data ¹H-NMR(CDCl₃): δ[ppm] |
|---|---|---|---|
| h | O | 3-Cl-phenyl | melting point: 45° C. |
| i | O | 2-CH₃-6-Cl-phenyl | melting point: 86° C. |
| k | O | —CH₂—CH₂—phenyl | 7.98(d, 1H), 7.1–7.45 (m, 8H), 4.35(t, 2H), 3.92 (s, 3H), 3.69(s, 2H), 2.92 (t, 2H) |
| l | O | cyclohexyl (H) | 7.98(d, 1H), 7.4–7.5 (m, 2H), 7.19(t, 1H), 4.75–4.85(m, 1H), 3.92 (s, 3H), 3.7(s, 2H), 1.15–1.87(m, 10H) |
| m | O | —CH(CH₃)-phenyl | 7.98(d, 1H), 7.21–7.39 (m, 7H), 7.19(t, 1H), 5.91(q, 1H), 3.92(s, 3H), 3.73(s, 2H), 1.52(d, 3H) |
| n | O | 3-N(CH₃)₂-phenyl | 8.0(d, 1H), 7.45–7.08 (m, 2H), 7.12–7.28(m, 2H), 6.55(dd, 1H), 6.38(dd, 1H), 6.3(t, 1H), 3.93(s, 5H), 2.90(s, 6H) |
| o | O | Et | 7.98(d, 1H), 7.38–7.51 (m, 2H), 7.22(t, 1H), 4.20 (q, 2H), 3.92(s, 3H), 3.71 (s, 2H), 1.25(t, 3H) |
| p | NH | phenyl | melting point: 133° C. |
| q | NH | 4-OCH₃-phenyl | melting point: 94° C. |
| r | NH | 3-OCH₃-phenyl | melting point: 110° C. |
| s | NH | 2,5-di-CH₃-phenyl | melting point: 122° C. |
| t | NH | 2,4-di-OCH₃-phenyl | 8.65(s, 1H), 8.02(d, 1H), 7.5(t, 1H), 7.32(d, 1H), 7.25(t, 1H), 6.74(d, 2H), 6.22(t, 1H), 3.96(s, 3H), 3.8(s, 2H), 3.75(s, 6H) |
| u | NH | 4-COOCH₃-phenyl | (measured in DMSO⁶-D): 7.92(t, 3H), 7.74(d, 2H), 7.18–7.32(m, 1H), 7.52–7.6(m, 2H), 3.96 (s, 2H), 3.85(s, 3H), 3.82(s, 3H) |

Preparation of S((2-carbomethoxyphenyl)-thioglycolyl chloride

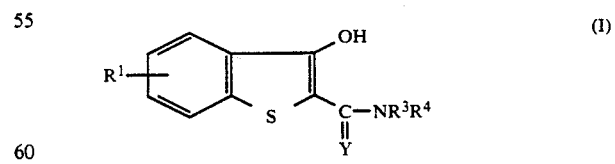

2.26 ml (10 mmol) of S-(2-carbomethoxyphenyl)thioglycolic acid. (obtained according to Friedländer, Liebigs Ann. Chem. 351, (1907) 390-420) are introduced into 20 ml of thionyl chloride and the mixture is heated under reflux for three hours. It is then evaporated in vacuo and the residue is subsequently distilled twice with dry toluene. It is finally dried by the oil pump. The residue is utilized further without further purification. It is a red oil which slowly solidifies to give a wax-like substance.

It will be appreciated that the instant specification is set forth by way of illustration and not limitation, and that various modifications and changes may be made without departing from the spirit and scope of the present invention.

What is claimed is:

1. A method of combating endoparasites in humans and animals which comprises administering to such humans and animals an endoparasiticidally effective amount of a 3-hydroxybenzothiophene of the formula $$\text{(I)}$$

in which
Y represents =O or =NH,
R¹ represents one or more identical or different radicals from the group consisting of hydrogen, alkyl, alkoxy, alkylthio, halogenoalkyl, halogenoalkoxy, halogenoalkylthio, alkylenedioxy, halogenoalkylenedioxy, halogen, CN, NO₂, NH₂, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, which, in turn, may again be substituted, $R^3$ represents hydrogen or alkyl, $R^4$ represents an alkyl or aralkyl carbocylic or heterocyclic aromatic radical or the radical $-COOR^5$, $R^3$ and $R^4$, together with the adjacent nitrogen atom, represent a 5- or 6-membered heterocycle which may contain O or N as further heteroatoms and is optionally substituted by $C_1$-$C_4$-alkyl, $C_1$-$C_4$-hydroxyalkyl, $C_1$-$C_4$-halogenoalkyl or $C_1$-$C_4$-alkoxyalkyl, or optionally substituted aryl, $R^5$ represents alkyl, cycloalkyl, aralkyl or aryl, which, in turn, may again be substituted.

2. The method according to claim 1, in which $R^1$ represents alkyl having 1 to 4 carbon atoms; alkoxy having 1 to 4 carbon atoms; alkylthio having 1 to 4 carbon atoms; halogenoalkyl having 1 to 4 carbon atoms and 1 to 5 halogen atoms, where the halogen atoms are identical or different; halogenoalkoxy having 1 to 4 carbon atoms and 1 to 5 halogen atoms; halogenoalkylthio having 1 to 4 carbon atoms and 1 to 5 halogen atoms; in the case of phenyl, represents alkylenedioxy having 1 or 2 carbon atoms; in the case of phenyl represents halogen-substituted alkylenedioxy having 1 or 2 carbon atoms and 1 to 4 halogen atoms; halogen; cyano; nitro; dialkylamino having 1 to 4 carbon atoms per alkyl group; alkylcarbonyl having 2-4 carbon atoms; carbalkoxy having 2 to 4 carbon atoms; alkylsulphonyl having 1 to 4 carbon atoms; arylsulphonyl having 6 or 10 aryl carbon atoms; phenyl, naphthyl, phenoxy, naphthoxy, phenylthio or naphthylthio, which in turn, may again be substituted, $R^3$ represents hydrogen or alkyl, $R^4$ represents $C_{1-4}$-alkyl, benzyl or phenyl which are optionally substituted by one of the radicals mentioned for $R^1$, or represents a radical of the formula $-COOR^5$, or $R^3$ and $R^4$, together with the adjacent nitrogen atom, represent a 5- or 6-membered heterocycle which may contain O, or N as further hetero atoms and is optionally substituted by $C_1$-$C_4$-alkyl, $C_1$-$C_4$-hydroxyalkyl, $C_1$-$C_4$-alkoxyalkyl or optionally substituted aryl, $R^5$ represent $C_1$-$C_4$-cycloalkyl, aralkyl or aryl which, in turn, may be substituted by one of the radicals mentioned under $R^1$, Y represents $=O$ or $=NH$.

3. The method according to claim 1, in which $R^1$ represents halogen, $C_1$-$C_4$-alkyl, $C_{1-4}$-alkoxy, $C_{1-4}$-halogenoalkoxy, $C_{1-4}$-halogenoalkylthio, phenyl which is optionally substituted by $C_1$-$C_4$-alkyl, $C_1$-$C_4$-alkoxy, $C_1$-$C_4$-halogenoalkoxy, $C_1$-$C_4$-halogenoalkylthio, $C_1$-$C_4$-alkylthio, halogenosulphonyl, $C_1$-$C_4$-alkylsulphonyl, $C_1$-$C_4$-halogenoalkylsulphonyl, $C_1$-$C_4$-halogenoalkyl, or methylenedioxy or ethylenedioxy which are optionally substituted by fluorine or chlorine, halogen, $NO_2$, or phenoxy which is optionally substituted by one of the abovementioned radicals, $R^3$ represents hydrogen, $R^4$ represents $C_{1-4}$-alkyl, benzyl or phenyl which are optionally substituted by one of the radicals mentioned for $R^1$ or represents a radical of the formula $-COOR^5$, or $R^3$ and $R^4$, together with the adjacent nitrogen atom, represent one of the radicals piperidino, morpholino, pyrolidino, N-methylpiperazino or 2,6-dimethylmorpholino or 2,6-diphenylmorpholino $R^5$ represents $C_{1-4}$-alkyl or benzyl, Y represents $=O$ or $=NH$.

4. The method according to claim 1, in which $R^1$ represents fluorine or chlorine, $NO_2$, $CF_3$, $CH_3$, $OCF_3$, $SCF_3$, $SCF_2Cl$, $OCH_3$, $OCF_2CF_2H$, $-CF_2CHFO-$, $-O-CH_2-O$ or $-O-CF_2-O$, $R^3$ represents hydrogen, $R^4$ represents methyl, ethyl, benzyl or phenyl which are optionally substituted by halogen, $C_{1-4}$-alkyl, $C_{1-4}$-halogenoalkyl, $C_{1-4}$-alkoxy, $C_{1-4}$-alkylmercapto, $C_{1-4}$-halogenoalkylmercapto, or $C_{1-4}$-alkoxycarbonyl, or represents the radical $-COOR^5$, or $R^3$ and $R^4$, together with the adjacent nitrogen atom, represent one of the radicals piperidino, morpholine 2,6-dimethylmorpholino or N-methylpiperazino, $R^5$ represents $C_{1-4}$-alkyl or benzyl, and Y represents $=O$ or $=NH$.

5. A method according to claim 1

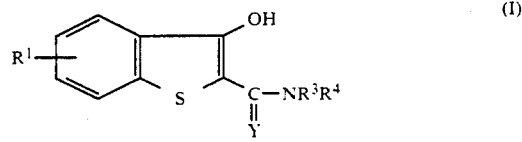

(I)

in which

Y represents $=O$ or $=NH$, $R^1$ represents one or more identical or different radicals from the group consisting of hydrogen, alkyl, alkoxy, alkylthio, halogenoalkyl, halogenoalkoxy, halogenoalkylthio, alkylenedioxy, halogenoalkylenedioxy, halogen, CN, $NO_2$, $NH_2$, alkylamino, dialkylamino, alkylcarbonyl, carbalkoxy, alkylsulphonyl, arylsulphonyl, sulphamoyl, alkylsulphamoyl, dialkylsulphamoyl, aryl, aryloxy and arylthio, which, in turn, may again be substituted, $R^3$ represents hydrogen or alkyl, and $R^4$ represents an alkyl, aralkyl, carbocyclic or heterocyclic aromatic radical, or $R^3$ and $R^4$, together with the adjacent nitrogen atom, represent a 5- or 6-membered heterocycle which may contain O or N as further hetero atoms and is optionally substituted by $C_1$-$C_4$-alkyl, $C_1$-$C_4$-hydroxyalkyl, $C_1$-$C_4$-halogenoalkyl or $C_1$-$C_4$-alkoxyalkyl or optionally substituted aryl.

* * * * *

UNITED STATES PATENT AND TRADEMARK OFFICE
CERTIFICATE OF CORRECTION

PATENT NO. : 5,118,680
DATED : June 2, 1992
INVENTOR(S) : Muller et al

It is certified that error appears in the above-indentified patent and that said Letters Patent is hereby corrected as shown below:

| | |
|---|---|
| Col. 5, line 24 | After " particular " insert -- 1 -- |
| Col. 31, lines 24 25 & 26 | Delete in the case of phenyl " |
| Col. 31, line 46 | After " hydroxyalkyl " insert -- $C_1$-$C_4$-halogenoalkyl -- |
| Col. 31, line 48 | After " represent " insert -- $C_1$-$C_4$-alkyl -- |
| Col. 31, line 48 | Delete " $C_1$-$C_4$ " and substitute -- $C_4$-$C_7$ -- |
| Col. 32, line 17 | Delete " -$CF_2$CHFO- " and substitute -- $OCF_2$CHFO- -- |
| Col. 32, lines 27-28 | Delete " morpholine " and substitute -- morpholino -- |

Signed and Sealed this

Tenth Day of May, 1994

Attest:

BRUCE LEHMAN

*Attesting Officer*   *Commissioner of Patents and Trademarks*